United States Patent
Neffgen

(10) Patent No.: US 6,255,407 B1
(45) Date of Patent: Jul. 3, 2001

(54) ONE-COMPONENT ADHESIVE

(75) Inventor: Stephan Neffgen, Hamburg (DE)

(73) Assignee: Ernst Muhlbauer KG, Hamburg (DE)

( * ) Notice: Subject to any disclaimer, the term of this patent is extended or adjusted under 35 U.S.C. 154(b) by 0 days.

(21) Appl. No.: 09/416,957

(22) Filed: Oct. 13, 1999

(30) Foreign Application Priority Data

Oct. 13, 1998 (DE) .............................................. 198 47 116
Oct. 29, 1998 (DE) .............................................. 198 49 966

(51) Int. Cl.⁷ .................................................... C08C 19/25
(52) U.S. Cl. ........................ 525/342; 525/106; 526/319; 526/279; 526/328.5; 526/329.7; 523/105
(58) Field of Search .................................... 525/342, 106; 526/319, 279, 328.5, 329.7; 523/105

(56) References Cited

U.S. PATENT DOCUMENTS 5,476,912 * 12/1995 Hosoi et al. .
5,789,485 * 8/1998 Kobayashi et al. .

FOREIGN PATENT DOCUMENTS 0 632 060   1/1995  (EP) .
0 685 547  12/1995  (EP) .
0 826 359   3/1998  (EP) .

* cited by examiner

*Primary Examiner*—Robert Dawson
*Assistant Examiner*—Kuo-Liang Peng
(74) *Attorney, Agent, or Firm*—Morrison & Foerster LLP

(57) ABSTRACT

The invention relates to an adhesive comprising a polymer having the following features:
- a polymeric backbone,
- alkyl, aryl and/or alkenyl groups attached to the backbone by way of ester linkages,
- alkyl and/or aryl spacer groups attached to the backbone by way of ester linkages,
- an open-chain and/or cyclic silicone group and/or silane group is attached to the spacer by means of an Si—C bond,
- an ethylene group is attached to the silicone and/or silane group by means of an Si—C bond,
- the ethylene group in turn is connected to a second silicone group which comprises M, D, T and/or Q silicone units and comprises at least one vinyl group attached to Si.

The adhesive of the invention is stable even under moist conditions and ensures good promotion of adhesion between a polymer and an organosilicon elastomer.

14 Claims, No Drawings

ONE-COMPONENT ADHESIVE

The invention relates to a polymeric adhesive according to the main claim, to processes for preparing it and to its use as a medical preparation and for preparing an adhesion promoter for use in the dental field.

Dental prostheses consist in general of a hard polymer; polymethyl methacrylate (PMMA) is used in many cases. In order to improve the accuracy of fit and to avoid pressure points on the oral mucosa, it may be necessary to provide such dental prostheses with relining material which stays permanently soft. Relining materials used include organopolysiloxanes (silicones). However, there are problems in establishing a permanent bond between the polymer of the prosthesis and the silicone relining material.

DE-A-44 14 837 describes an adhesion promoter for producing a bond between PMMA and an organosilicon elastomer. First of all a two-component polyurethane reactive adhesive is applied to the prosthesis polymer and, after a certain curing time, is provided with a film of organohydrogen-silicone fluid. The relining material is applied to this film. Applying a multi-component adhesion promoter of this kind is complex and laborious.

One-component adhesives are disclosed in EP-A-0 632 060 and EP-A-0 826 359. It has been found, however, that the adhesives disclosed therein are sensitive to hydrolysis, and lack stability. Adhesion promoter systems are known, furthermore, from DE-A-195 39 653, EP-A-0 685 547, EP-A-0 384 401, EP-A-0 731 143 and U.S. Pat. No. 5,635, 578.

The object of the present invention is to provide an adhesive of the type specified at the outset which is able to produce good adhesion between a polymer and an organo-silicone material, is simple and quick to apply, and is chemically stable.

This object is achieved in accordance with the invention by means of an adhesive which comprises a polymer having the following features:
- a polymeric backbone,
- alkyl, aryl and/or alkenyl groups attached to the backbone by way of ester linkages,
- alkyl and/or aryl spacer groups attached to the backbone by way of ester linkages,
- an open-chain and/or cyclic silicone group and/or silane group is attached to the spacer by means of an Si—C bond,
- an ethylene group is attached to the silicone and/or silane group by means of an Si—C bond,
- the ethylene group in turn is connected to a second silicone group which comprises M, D, T and/or Q silicone units and comprises at least one vinyl group attached to Si.

The adhesive of the invention comprises a polymeric backbone. This backbone can, for example, be a poly(alk)acrylate. This terminology includes polyacrylates and polyalkacrylates such as, for example, polymethacrylate.

Alkyl and/or aryl groups (this terminology includes aralkyl groups) are connected as alcohol components to the backbone by way of ester linkages. These alkyl and/or aryl groups may carry additional functional groups such as, for example, hydroxyl groups. The specified alcohol components are preferably esters of methanol, ethanol, propanol, isopropanol, butanol, tert-butanol, pentanol, hexanol, cyclohexanol, octanol, decanol, lauryl alcohol, cetyl alcohol, propynyl alcohol, glycerol, diethylene glycol, triethylene glycol, benzyl alcohol and its derivatives, phenol and its derivatives, 2-hydroxyethoxybenzene and 2-hydroxyethylbenzene, the ester linkage being made with an acid function or acid derivative function on the backbone.

Likewise attached to the backbone by way of ester linkages are branched or unbranched alkyl and/or aryl groups, which act as a spacers. Preferred spacers used are straight-chain, unbranched alkyl chains having a chain length from $C_3$ to $C_{18}$, with particular preference $C_3$ and $C_6$ to $C_{18}$. The spacer may comprise functional groups such as, for example, ester groups, ether functions or additional double bonds.

Attached to the spacer by means of a stable Si—C bond is an open-chain and/or cyclic silicone group (an organosiloxane) and/or a silane group. The term silicone group includes any group containing at least one siloxane bond (Si—O—Si bond).

Likewise attached to this extended spacer by means of stable Si—C bond is an ethylene group, which in turn is connected to a second silicone group which comprises M, D, T and/or Q silicone units and also at least one ethylenically unsaturated group (vinyl group) attached to an Si atom. The terminology M, D, T and Q to denote silicone units is an international convention (see, for example, ROmpp Chemielexikon, 9th Edition, Vol. 9, p. 4168) and denotes silicone units having the following structures:

M:

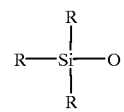

D:

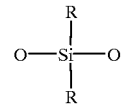

T:

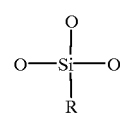

Q:

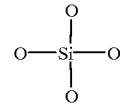

The radical R denotes alkyl, aryl or aralkyl groups.

In accordance with the invention, the said second silicone group comprises at least one ethylenically unsaturated group attached to Si. By means of this reactive double bond arranged on the second silicone group, the adhesive is able to establish a chemical bond to the organosilicon elastomer.

The adhesive according to the invention has two essential advantages over the prior art. Firstly, the silicone units of the adhesive include, as the reactive group, ethylenically unsaturated double bonds and no Si—H bonds. Since the Si—H bond is able to react with nucleophiles, the adhesive of the invention is substantially more stable (especially on storage).

Linkage between the backbone and the silicone groups is exclusively by way of stable Si—C bonds, and not by way of hydrolysis-sensitive Si—O—C bonds.

The open-chain and/or cyclic silicone group attached to the spacer has preferably one silane unit and/or from 1 to 10, with particular preference from 1 to 5, silicone units (Si—O units), which can be in a linear, branched and/or cyclic arrangement. Alkyl, aryl and/or aralkyl side groups can be present, preference being given to methyl, ethyl, phenyl and benzyl groups.

The adhesive preferably has the following structural elements:

a)
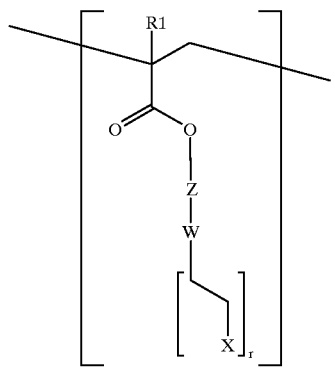

b)
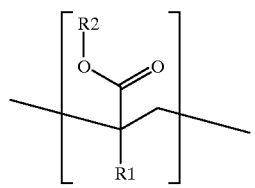

in which r is an integer from 1 to 3, $R_1$ is identical or different and is H, methyl, ethyl, propyl or butyl, $R_2$ is a straight-chain or branched alkyl, aryl, aralkyl and/or alkenyl group, Z is a straight-chain or branched alkyl or aryl or aralkyl group, W is an open-chain and/or cyclic silicone group or silane group which is attached by way of Si—C bonds, X is a second silicone group containing M, D, T and/or Q units, at least one silicone group X containing at least one vinyl group attached to Si.

The said structural elements a) and b) can be arranged in alternation or at random in the backbone. As evident from the formula a), the silicone group W can contain between 1 and 3 second silicone group(s) attached by way of an ethylene group and having at least one vinyl group.

The structural element a) can have the following the composition:

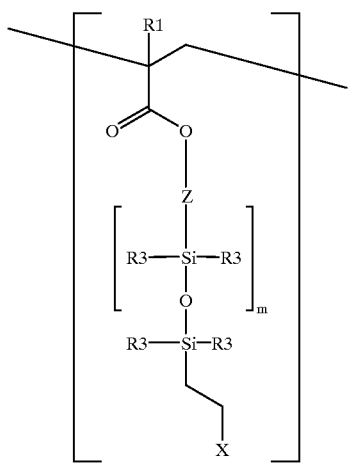

in which $R_1$, $R_2$, Z and X are as defined in claim 2, $R_3$ is a straight-chain or branched alkyl or aryl or aralkyl group and m is an integer from 0 to 2.

The backbone can feature a poly(alk)acrylate, especially poly(meth)acrylate. Where the invention uses the expression acrylate or polyacrylate, this always includes polyalkacrylates which carry an alkyl group, such as for example a methyl group, on the α carbon atom. The poly(alk)acrylate component can have a molecular weight of between 800 and 1,000,000. Preference is given to molar masses of between 5000 and 500,000, with particular preference between 20,000 and 250,000.

Instead of a pure poly(alk)acrylate the backbone can also be a copolymer of (alkyl) acrylates and other unsaturated esters.

The silicone group (X in claim 2) intended for connection to the organosilicon elastomer preferably has a molecular weight of between 80 and 200,000. Where two or more silicone groups X are attached to the open-chain or cyclic silicone unit (W in claim 2), the stated molar mass figure relates to one of these silicone groups. Not every silicone group X present in the form of a side chain of the silicone group W need necessarily have a reactive vinyl group, although at least one silicone group X has at least one reactive vinyl group.

The spacer (Z in claim 2) is preferably a straight-chain, i.e. unbranched, alkyl compound.

The adhesive of the invention may additionally comprise a non-reactive solvent. Non-reactive means that the solvent shows essentially chemically inert behaviour under the storage and service conditions of the adhesive. Examples of suitable solvents are ethyl acetate, toluene, benzene, methylene chloride, chloroform, isobutanol, isopropanol, ethanol, methanol, cyclohexanol, cyclohexanone, acetone, tetrahydrofuran, cyclohexyl acetate, acetic acid, methyl ethyl ketone, diethyl ether, or mixtures thereof.

The adhesive may additionally comprise reactive (meth) acrylic resins. As already explained above, this terminology includes acrylate resins and methacrylate resins. Examples of suitable (meth)acrylate resins are ethylene glycol di(meth)acrylate, diethylene glycol di(meth)acrylate, triethylene glycol di(meth)acrylate, tetraethylene glycol di(meth) acrylate, hexanediol di(meth)acrylate, butanediol di(meth) acrylate, dodecanediol di(meth)acrylate, 2,2,-bis[p-

(hydroxy-(meth)acryloyloxy)phenyl]propane, ethoxylated bisphenol A di(meth)acrylate, hydroxyethyl (meth)acrylate, hydroxypropyl (meth)acrylate, glycerol di(meth)acrylate, urethane di(meth)acrylate, urethane polyester di(meth) acrylate, trimethylolpropane tri(meth)acrylate and dipentaerythritol penta(meth)acrylate.

The adhesive may additionally comprise amorhous silicas, silicates, finely divided glasses and/or quartzes and/or pigments for colouring. Mention may be made of silanized Aerosils by way of example.

has more than two Si—H bonds, it is possible under certain circumstances for two or more silicone groups X to be attached to a vinyl group by addition reaction of an Si—H bond. In this case, r in claim 2 is greater than 1. The second silicone groups attached in the last reaction step each still contain, at least in part, a free vinyl group, which serves to attach the adhesive to an organosilicon elastomer.

The prepared adhesive according to the invention can in this case have the following structure:

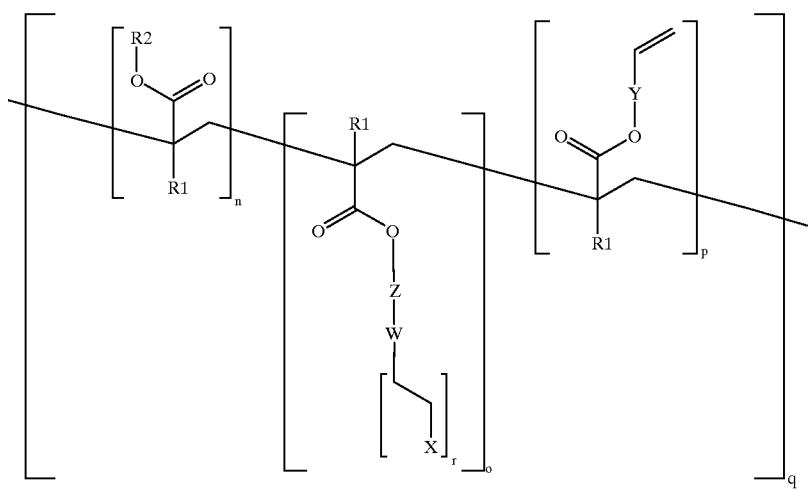

The invention further relates to a process for preparing such an adhesive, comprising the steps of:
  transesterifying a poly(alk)acrylate with ethylenically unsaturated alcohols,
  reacting this compound with volatile silanes and/or siloxanes containing at least one and, at least in part, at least two Si—H bonds,
  reacting the reaction product with silicones which contain at least one Si-bonded vinyl group and, at least in part, two or more Si-bonded vinyl groups.

In the first step of the preparation, a polymeric acrylate or alkacrylate (e.g. methacrylate) is reacted with ethylenically unsaturated alcohols. In this step, using the terminology of claim 2, the group $R_2$ attached to the backbone via an ester linkage is replaced by a spacer Z. Preferably, the complete transesterification of all ester groups on the backbone does not take place, and so, preferably, a certain fraction of ester groups $R_2$ remains in the polymer.

In the next step, the resulting compound is reacted with volatile silanes and/or siloxanes having at least 2 Si—H bonds. In this case, an Si—H bond reacts with the ethylenically unsaturated group of the spacer Z, so that the silicone group W is attached to the spacer Z. This reaction can be carried out such that almost all of the ethylenically unsaturated ester groups react with the silanes; alternatively, however, it is also possible for ethylenically unsaturated esters to remain in the polymer.

In the third step, the reaction product is reacted with silicones which contain, at least in part, two or more Si-bonded ethylenically unsaturated groups. The Si—H bond of the first silicone group W, which is still present, reacts in this case with a vinyl group of the attaching second silicone group X (in each case in the terminology of claim 2). If the volatile silane attached in the second reaction step The formula unit n is an original poly(alkyl)acrylate which still carries the original ester group. The formula unit p shows a polyacrylate building block to which an alkenyl group is linked by way of the ester. Y here is a straight-chain or branched alkyl or aryl or aralkyl group. In the case of the unit o, on the other hand, a silane or siloxane group is attached by way of the group Z, and via the group W carries at least one silicone group X. At least one silicone group X has at least one Si-bonded vinyl group. In an adhesive according to the invention, a formula unit p need not necessarily be present. The sequence of the formula units n and o within one unit q is arbitrary and can be different; however, both units n and units o must be present in the adhesive.

A second process according to the invention for preparing an adhesive according to the invention comprises the following steps:
  reacting a copolymer of alkyl (meth)acrylates and alkenyl (meth)acrylates with volatile silanes and/or siloxanes which contain at least one and, at least in part, at least two Si—H bonds,
  reacting the reaction product with silicones which contain at least one Si-bonded vinyl group and, at least in part, two or more Si-bonded groups.

The starting polymer used in this case is a copolymer of alkyl (meth)acrylates and alkenyl (meth)acrylates which from the outset includes reactive double bonds onto which Si—H bonds of silanes can be addition-reacted. When a copolymer of this kind is used it is unnecessary to provide the polymer with such reactive double bonds first of all by transesterification of ethylenically unsaturated alcohols. In a first step, volatile silanes having at least two Si—H bonds are addition-reacted onto the reactive double bonds of the copolymer. In a second step, this reaction product is reacted with silicones which contain at least two Si-bonded vinyl groups. The two reaction steps correspond to the second and third reaction steps of the abovementioned first process according to the invention.

The invention relates, furthermore, to an adhesive defined in the claims for use as a medical preparation, and to the use of this adhesive for preparing an adhesion promoter for use in the dental field for the purpose of producing a frictional bond between an adhesive and an organosiloxane material.

The adhesive of the invention can be applied directly to a polymer. Where the said adhesive includes a solvent, this solvent can be evaporated. Subsequently, an organosilicon elastomer is applied to the adhesive film.

An adhesion promoter prepared in accordance with the invention can be used, for example, for connection between a dental prosthesis comprising a hard polymer, and an organosilicon relining material. A further possible application is the promotion of adhesion between an individual impression tray, made of polymer, and an impression material.

This adhesive can likewise be used in otoplasty, for example for connecting earshells to a relatively soft silicone liner or else for frictional connection to other silicone components such as, for example, hoses. The earshells concerned can be, for example, hearing-aid components made from a hard polymer.

Exemplary embodiments of the invention are described below. Unless specified otherwise, all compositions are stated in weight fractions. Viscosities were measured at a temperature of 25° C.

Materials

The starting materials described below were used in the preparation of the adhesion promoter systems:

TABLE 1

| | |
|---|---|
| PA-30 | Poly(methyl methacrylate) with relatively small fractions of acrylate comonomer; molar mass ≈ 30,000 |
| PA-180 | Poly(methyl methacrylate) with relatively small fractions of acrylate comonomer; molar mass ≈ 180,000 |
| DVPDMS | Linear α,ω-divinylpoly(dimethyl-siloxane); η ≈ 25 mPa · s; vinyl content ≈ 1 mmol $g^{-1}$ |
| VMQS | Branched vinyl-containing poly(siloxane); η ≈ 200 mPa · s; vinyl content ≈ 0.8 mmol $g^{-1}$ |
| VMDTS | Branched vinyl-containing poly(siloxane); η ≈ 490 mPa · s; vinyl content ≈ 1.1 mmol $g^{-1}$ |
| TMDS | 1,1,3,3-tetramethyldisiloxane |
| Pt catalyst | $Pt^0$ complex with 1,3-divinyl-1,1,3,3-tetra-methyldisiloxane; 10.7% strength solution in toluene |

EXAMPLE 1

Preparation of a Transesterification Catalyst 2 parts of titanium tetraisopropoxide are dissolved in 5.5 parts of dried 9-decen-1-ol with exclusion of moisture. Subsequently, 0.05 part of 2,6-di-tert-butyl-4-methylphenol is added and the mixture is reacted with stirring at 70° C. under about 20 mbar for 4 h. The product is used without further purification in the subsequent steps.

EXAMPLE 2

Preparation of a Vinyl-modified Polymethyl Methacrylate (VPA 1)

100 parts of dry polymethyl methacrylate PA-180 (copolymer with relatively small fractions of other acrylates) are dissolved in about 350 parts of dry toluene with exclusion of moisture, and this solution is admixed with 0.03–0.04 part of 2,6-di-tert-butyl-4-methylphenol and with 1.94 parts of 9-decen-1-ol and 2.13 parts of the catalyst from Example 1. The mixture is stirred until homogeneous and then freed from solvent by vacuum distillation. The residue is reacted at 160° C. under a nitrogen atmosphere for 6.5 h. Any condensate is removed by distillation or stripped off under a rough vacuum. The crude product is dissolved in toluene and purified by precipitation in ethanol followed by filtration and vacuum drying of the precipitated product. The bromene number is 2.8.

EXAMPLE 3

Preparation of a Vinyl-modified Polymethyl Methacrylate (VPA 2)

100 parts of dry polymethyl methacrylate PA-180 (copolymer with relatively small fractions of other acrylates) are dissolved in about 350 parts of dry toluene with exclusion of moisture, and this solution is admixed with 0.03–0.04 part of 2,6-di-tert-butyl-4-methylphenol and with 1.55 parts of 9-decen-1-ol and 1.7 parts of the catalyst from Example 1. The mixture is stirred until homogeneous and then freed from solvent by vacuum distillation. The residue is reacted at 160° C. under a nitrogen atmosphere for 5.5 h. Any condensate is removed by distillation or stripped off under a rough vacuum. The crude product is dissolved in toluene and purified by precipitation in ethanol followed by filtration and vacuum drying of the precipitated product. The bromene number is 1.6.

EXAMPLE 4

Preparation of a vinyl-modified polymethyl methacrylate (VPA 3)

100 parts of dry polymethyl methacrylate PA-30 (copolymer with relatively small fractions of other acrylates) are dissolved in about 350 parts of dry toluene with exclusion of moisture, and this solution is admixed with 0.03–0.04 part of 2,6-di-tert-butyl-4-methylphenol and with 1.55 parts of 9-decen-1-ol and 1.7 parts of the catalyst from Example 1. The mixture is stirred until homogeneous and then freed from solvent by vacuum distillation. The residue is reacted at 160° C. under a nitrogen atmosphere for 5.5 h. Any condensate is removed by distillation or stripped off under a rough vacuum. The crude product is dissolved in toluene and purified by precipitation in ethanol followed by filtration and vacuum drying of the precipitated product. The bromene number is 2.1.

EXAMPLE 5

Preparation of a Polysiloxane-modified Polymethyl Methacrylate 100 parts of dry vinyl-modified poly(methyl methacrylate) from Example 2 are dissolved in about 2500 parts of dry toluene with exclusion of moisture and then admixed, with stirring, with 33.5 parts of TMDS and 10 parts of Pt catalyst solution. The mixture is stirred at 65° C. for 7 h. About 80% of the solvent is distilled off in vacuo and then replaced by dry toluene. 255 parts of DVPDMS are added with stirring and the mixture is stirred at 70° C. for a period of 7 h. The reaction product is precipitated from hexane, isolated and dried in vacuo.

EXAMPLE 6

Preparation of a Polysiloxane-modified Polymethyl Methacrylate 100 parts of dry vinyl-modified poly(methyl methacrylate) from Example 3 are dissolved in about 2500 parts of dry toluene with exclusion of moisture and then admixed, with stirring, with 27 parts of TMDS and 10 parts of Pt catalyst solution. The mixture is stirred at 65° C. for 7 h. About 80% of the solvent is distilled off in vacuo and then replaced by dry toluene. 252 parts of VMQS are added with stirring and the mixture is stirred at 70° C. for a period of 7 h. The reaction product is precipitated from hexane, isolated and dried in vacuo.

EXAMPLE 7

Preparation of a Polysiloxane-modified Polymethyl Methacrylate 100 parts of dry vinyl-modified poly(methyl methacrylate) from Example 4 are dissolved in about 2500 parts of dry toluene with exclusion of moisture and then admixed, with stirring, with 27 parts of TMDS and 10 parts of Pt catalyst solution. The mixture is stirred at 65° C. for 7 h. About 80% of the solvent is distilled off in vacuo and then replaced by dry toluene. 182 parts of VMDTS are added with stirring and the mixture is stirred at 70° C. for a period of 7 h. The reaction product is precipitated from hexane, isolated and dried in vacuo.

The adhesives prepared in accordance with Examples 5 to 7 are subjected to the following test procedure. The adhesion promoter polymer (adhesive) is first of all dissolved in ethyl acetate in a concentration of 5% by weight. The resultant solution is used to thinly coat an area of 30×20 mm² of a polyacrylate plate (Paladon 65, from Kulzer) measuring 60×20 mm², which was wet-sanded beforehand (abrasive grade 500) and cleaned with ethanol, coating being carried out once starting from one end of the plate. After an evaporation period of 1 minute, a layer 4 mm thick of a silicone material which undergoes addition crosslinking at room temperature (Mollosil Plus, from Detax) is applied to the entirety of the polyacrylate support prepared in the preceding step. 1 h after hardening of the silicone, the arrangement is subjected to a 90° peel test starting from the non-adhering section (the section not coated with adhesion promoter) of the polyacrylate support. The adhesion is assessed qualitatively in accordance with the following scheme:

A: complete cohesive failure of the silicone; the adhesion exceeds the tensile strength of the silicone B: adhesive failure with perceptible adhesion; the adhesion is weaker than the tensile strength of the silicone C: no adhesion The results of the experiments are summarized in Table 2

TABLE 2

| Adhesion promoter from | Storage in water (40° C.) | Adhesion |
|---|---|---|
| Example 5 | — | A |
| Example 6 | — | B |
| Example 7 | — | A |
| Example 7 | 24 h | A |
| PA-30 (Comparative Example) | — | C |
| VPA-3 (Comparative example) | — | C |

The results show that the adhesives of the invention ensure stable adhesion of the silicone to the polymer even under wet conditions.

What is claimed is:

1. A medical adhesive composition comprising a polymer, wherein the polymer has:

a polymeric backbone, alkyl, aryl and/or alkenyl groups attached to the backbone by way of ester linkages, alkyl and/or aryl spacer groups attached to the backbone by way of ester linkages, an open-chain and/or cyclic silicone group and/or silane group attached to the spacer by means of an Si—C bond, an ethylene group is attached to the silicone and/or silane group by means of an Si—C bond, wherein the ethylene group in turn is connected to a second silicone group which comprises M, D, T and/or Q silicone units and comprises at least one vinyl group attached to Si.

2. A medical adhesive composition according to claim 1, wherein the polymer has the following structural elements:

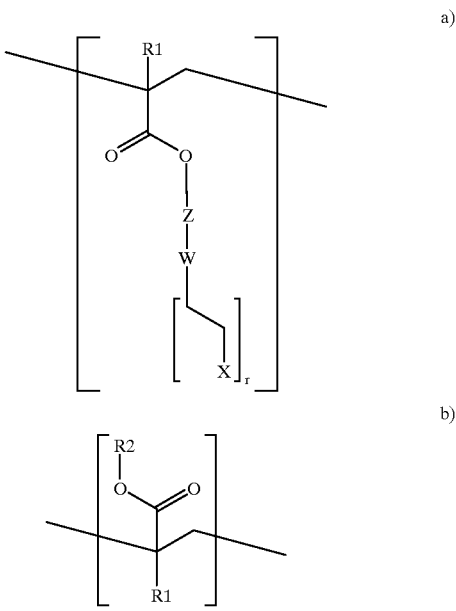

in which r is an integer from 1 to 3, $R_1$ is identical or different and is H, methyl, ethyl, propyl or butyl, $R_2$ is a straight-chain or branched alkyl, aryl, aralkyl and/or alkenyl group, Z is a straight-chain or branched alkyl or aryl or aralkyl group, W is an open-chain and/or cyclic silicone group or silane group which is attached by way of Si—C bonds, X is a second silicone group containing M, D, T and/or Q units, at least one silicone group X containing at least one vinyl group attached to Si.

3. A medical adhesive composition according to claim 2, wherein structural element a) has the following composition:

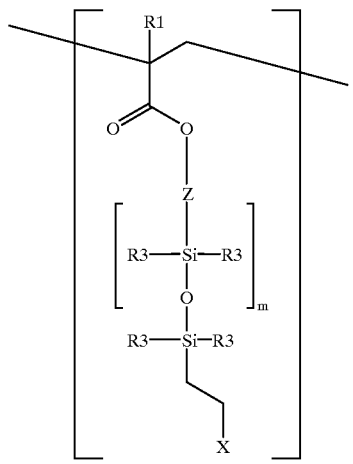

in which $R_1$, $R_2$, Z and X are as defined in claim 2, $R_3$ is a straight-chain or branched alkyl or aryl or aralkyl group and m is an integer from 0 to 2.

4. A medical adhesive composition according to claim 1, wherein the backbone comprises a poly(meth)acrylate.

5. A medical adhesive composition according to claim 4, wherein the poly(meth)acrylate component has a molecular weight of 800–1,000,000.

6. A medical adhesive composition according to claim 2, wherein the silicone group X has a molecular weight of 80–200,000.

7. A medical adhesive composition according to claim 2, wherein each silicone group X contains at least one vinyl group.

8. A medical adhesive composition according to claim 2, wherein the spacer Z is a straight-chain (unbranched) alkyl group.

9. A medical adhesive composition according to claim 1, further comprising a nonreactive solvent.

10. A medical adhesive composition according to claim 1, further comprising one or more reactive (meth)acrylate resins.

11. A medical adhesive composition according to claim 1, further comprising amorphous silica and/or finely divided glasses.

12. A medical adhesive composition according to claim 1, further comprising pigments.

13. Process for preparing an adhesive according to claim 1, comprising the steps of:
- transesterifying a poly(alk)acrylate with ethylenically unsaturated alcohols,
- reacting this compound with volatile silanes and/or siloxanes containing at least one and, at least in part, at least two Si—H bonds,
- reacting the reaction product with silicones which contain at least one Si-bonded vinyl group and, at least in part, two or more Si-bonded vinyl groups.

14. Process for preparing an adhesive according to claim 1, comprising the steps of:
- reacting a copolymer of alkyl (meth)acrylates and alkenyl (meth)acrylates with volatile silanes and/or siloxanes which contain at least one and, at least in part, at least two Si—H bonds,
- reacting the reaction product with silicones which contain at least one Si-bonded vinyl group and, at least in part, two or more Si-bonded vinyl groups.

\* \* \* \* \*